United States Patent
Albrecht et al.

(10) Patent No.: US 6,840,948 B2
(45) Date of Patent: Jan. 11, 2005

(54) DEVICE FOR REMOVAL OF TISSUE LESIONS

(75) Inventors: Thomas E. Albrecht, Cincinnati, OH (US); John A. Hibner, Mason, OH (US); Elizabeth L. Sebern, Cincinnati, OH (US)

(73) Assignee: Ethicon-Endo Surgery, Inc., Cincinnati, OH (US)

( * ) Notice: Subject to any disclaimer, the term of this patent is extended or adjusted under 35 U.S.C. 154(b) by 11 days.

(21) Appl. No.: 10/163,706

(22) Filed: Jun. 6, 2002

(65) Prior Publication Data

US 2003/0229343 A1 Dec. 11, 2003

(51) Int. Cl.⁷ ........................... A61B 18/28; A61B 17/32
(52) U.S. Cl. ..................... 606/170; 606/48; 600/564; 600/568
(58) Field of Search ............... 606/48, 32, 33, 606/41, 45, 110, 111, 113, 127, 128, 169, 166, 114, 159; 600/471, 564, 567, 568

(56) References Cited

U.S. PATENT DOCUMENTS

| | | | |
|---|---|---|---|
| 5,653,684 A | * | 8/1997 | Laptewicz et al. ............ 604/22 |
| 5,782,775 A | | 7/1998 | Milliman et al. |
| 5,794,626 A | | 8/1998 | Kieturakis |
| 5,895,392 A | * | 4/1999 | Riek et al. .................. 606/114 |
| 6,022,362 A | | 2/2000 | Lee et al. |
| 6,045,566 A | * | 4/2000 | Pagedas ...................... 606/167 |
| 6,221,006 B1 | * | 4/2001 | Dubrul et al. .............. 600/159 |
| 6,241,727 B1 | * | 6/2001 | Tu et al. ....................... 606/41 |
| 6,331,166 B1 | * | 12/2001 | Burbank et al. ............ 600/567 |

FOREIGN PATENT DOCUMENTS

| | | |
|---|---|---|
| WO | WO 99/04704 | 4/1999 |
| WO | WO 99/44506 | 10/1999 |

OTHER PUBLICATIONS

U.S. Appl. No. 10/164,199 filed Jun. 6, 2002.

* cited by examiner

*Primary Examiner*—David O. Reip
*Assistant Examiner*—D. Jacob Davis

(57) ABSTRACT

An excisional biopsy device and method are disclosed. The device can include a probe housing having a rotatable RF loop cutter mounted at the distal end of the probe, and the RF loop cutter can include at least one electrode supplied with an RF actuating signal for cutting tissue. A rotational drive and specimen containment sheath can also be included.

12 Claims, 7 Drawing Sheets

DEVICE FOR REMOVAL OF TISSUE LESIONS

BACKGROUND OF THE INVENTION

1. Field of the Invention

The present invention relates generally to the field of minimally invasive, image-guided excisional biopsy devices and processes, and more particularly pertains to an RF loop probe and process useful for excision and removal of cancerous lesions from soft tissue, including breast tissue and other other types of soft tissue such as the liver and the lungs.

2. Background of the Invention

The subject invention provides for removal of benign and malignant neoplasms of the breast in a less invasive manner than current surgical methods. Once a lesion is detected through either a physical exam or a mammogram, a biopsy is performed to diagnose whether the detected abnormality is malignant or benign. The tissue for this diagnostic biopsy can be acquired through a fine needle aspiration, core biopsy, vacuum-assisted core biopsy, or an open surgical biopsy. The tissue is then examined by a pathologist to determine whether the lesion is benign or malignant. If the lesion is determined to be benign, the patient may desire that the lesion be removed, especially if the lesion is palpable. If the lesion is malignant, the patient currently has two primary treatment options, 1) mastectomy or 2) breast conserving therapy, i.e. lumpectomy, followed by radiation therapy.

Breast conserving therapy is indicated for patients with Stage T1 or T2 cancers, which are less than 5 cm in greatest dimension. To localize the lesion within the breast, a radiologist places a guide wire under x-ray or ultrasound guidance, ideally with the distal tip of the guidewire in the center of the lesion and the proximal end of the wire protruding from the breast. The patient is then transported to the operating room. The surgeon uses the guidewire to find the lesion in the breast and to excise a lump of tissue including the cancer and a margin of normal tissue surrounding the cancer. Typically the surgeon uses a scalpel and/or an electrosurgical probe to cut a one-piece specimen and manage bleeding. The lump is removed and transported to the pathologist, who examines the margins of the specimen to determine whether the cancer has been completely removed. If the pathologists finds cancer cells too close to the edge of the specimen, he or she will recommend a re-excision, and the patient must have a second open surgical procedure to remove more tumor.

There are several problems with conventional breast conserving therapy which the present invention addresses. The first is localization of the lesion, i.e. needle localization. Because of technical challenges associated with placement of the needle, often the radiologist does not place the guide wire through the center or the lesion. It is particularly difficult to place the needle at the correct depth. Also, when the guidewire is placed under x-ray guidance, the breast is compressed. When the breast is decompressed for the open surgical excision, the guidewire can migrate in the breast, resulting in inaccurate placement thereof. Finally, the guidewire placement procedure is uncomfortable to the patient and logistically challenging because the procedure must be coordinated with the time of surgery. Often, the easiest path for the radiologist to place the guidewire is different from the best surgical approach, so the surgeon cannot follow the guidewire down to the lesion.

A second problem with current open lumpectomy is the highly variable re-excision rate, which can be anywhere from 5% to 50% depending upon the surgeon, the disease stage, and whether the lesion is diagnosed as malignant before the surgery. This high re-excision rate can be prescribed to the uncertain nature of the location of cancerous vs. healthy tissue. This uncertainty is a result of inaccurate guidewire placement and difficulty discerning the full extent of the disease, especially with non-palpable lesions. To compensate for the imprecision in determining the extent of the disease, the surgeon must take much more tissue than would be required if the full extent of the cancer could be imaged in real-time. The surgeon must also make a large incision to provide access for his/her hands and scalpel to excise the lesion. This results in a large scar and a great amount of tissue being removed, which both negatively impact cosmesis.

Finally, because the procedure is so invasive, the surgery must be performed in an operating room, resulting in higher overhead costs. The patient must be anesthetized with either conscious sedation and local anesthesia or general anesthesia, which can lead to further complications.

SUMMARY OF THE INVENTION

The present invention provides an RF loop probe for removal of a lesion from tissue, and comprises a probe housing having a rotatable RF loop cutter mounted at the distal end of the probe. The RF loop cutter comprises at least one electrode supplied with an RF actuating signal for cutting and tunneling of the probe, and a rotational drive for rotationally driving the RF loop cutter during a rotational cut around a tissue specimen containing the lesion. A specimen containment sheath is stored within the probe housing and attached to the rotatable RF loop cutter. The specimen containment sheath is deployed by the RF loop cutter as it is rotated to perform a rotational cut, such that the specimen containment sheath is drawn around the tissue specimen as the RF loop cutter rotationally cuts around the specimen.

In greater detail, the rotational drive comprises first and second drive electrical cables which are mechanically displaced to rotate the RF loop cutter, and the drive electrical cables also conduct RF electrical signals to the RF loop cutter. The RF loop cutter comprises a semicircular RF loop which cuts a spherical tissue specimen. After the RF loop cutter fully cuts around the spherical specimen, a draw cord is used to pull the containment sheath taut around the spherical specimen, to reduce its spherical volume to aid in its removal from the tissue and to prevent cancer cell displacement during removal.

The RF loop probe is preferably used with real-time imaging to assist in placement of the probe, and to more accurately assess a desired excision volume. The probe housing defines vacuum channels to provide a vacuum counter traction or immobilization of the adjacent tissue during cutting, and to remove fluids, and the vacuum channels also serve to house the first and second drive electrical cables which are mechanically displaced to rotate the RF loop cutter, and also conduct RF electrical signals to the RF loop cutter.

The RF loop probe comprises a disposable probe which is mounted to a reusable handpiece. The rotational drive includes a rotatable engagement shaft on the handpiece which engages a rotatable engagement shaft on the disposable probe which rotates a lead screw. The lead screw axially translates a carriage in the probe housing from a distal position to a proximal position in the probe housing, and the translating carriage pulls the drive electrical cables which rotate and supply an RF electrical signal to the RF loop cutter.

Each of the first and second drive electrical cables is an insulated wire which conducts at least one RF electrical signal to a different side of the RF loop cutter, and each drive electrical cable can conduct a separate independent RF electrical signal to a different side of the RF loop cutter.

Each drive electrical cable is wrapped around a drive spool to rotate the RF loop cutter. The probe housing defines diametrically-opposed legs which mount diametrically-opposed spools which are attached to the drive electrical cables and rotate the RF loop cutter as the drive electrical cables are drawn proximally. The RF loop cutter can comprise a tunneling electrode and a separate rotational cutting electrode, wherein the tunneling electrode and the rotational cutting electrode are bonded with an insulating material therebetween so that each of the two electrodes is energized independently of the other electrode. Alternatively, the RF loop cutter can comprise a single cutting electrode which provides both tunneling cutting and circular cutting.

In a first embodiment, the RF loop cutter has a semicircular shape, and the semicircular shaped RF loop cutter is positioned flat relative to the direction of insertion of the RF probe. In a second embodiment, the RF loop cutter has a semicircular shape, and the semicircular shaped RF loop cutter is positioned orthogonally relative to the direction of insertion of the RF probe. In one embodiment, the rotational drive includes a rotational worm gear which drives a gear attached to the RF loop to rotate the RF loop.

The present invention also provides a process or procedure for removal of a lesion from tissue which comprises inserting an RF loop probe into tissue of a patient in proximity to the lesion, the RF loop probe having a probe housing with a rotatable RF loop cutter with at least one electrode mounted at the distal end of the probe. During the step of inserting, supplying at least one electrode with an RF actuating signal for tunneling of the probe. After the probe is properly positioned relative to the lesion, rotationally driving the RF loop cutter during a rotational cut around a tissue specimen containing the lesion. During the step of rotational driving, deploying a specimen containment sheath stored within the probe housing and attached to the rotatable RF loop cutter, and supplying the at least one electrode with an RF actuating signal for cutting by the probe. In these steps, the specimen containment sheath is drawn around the tissue specimen as the RF loop cutter rotationally cuts around the specimen.

In greater detail, the process includes mechanically displacing first and second drive electrical cables to rotate the RF loop cutter, and also conducting RF electrical signals to the RF loop cutter through the drive electrical cables. The process includes rotating a semicircular RF loop cutter to cut around a spherical tissue specimen, and pulling the containment sheath by the RF loop cutter to surround the spherical tissue specimen. After the RF loop cutter fully cuts around the spherical specimen, pulling a draw cord to pull the containment sheath taut around the spherical specimen, to reduce its spherical volume to aid in its removal from the tissue and to prevent cancer cell displacement during removal.

Real-time imaging is preferably used with the RF loop probe to assist in placement of the probe, and to more accurately assess a desired excision volume.

The process includes applying a vacuum through vacuum channels in the probe housing to provide counter traction during cutting, and mechanically displacing the first and second drive electrical cables in the vacuum channels to rotate the RF loop cutter. A lead screw is rotated to axially translate a carriage in the probe housing from a distal position to a proximal position in the probe housing, with the translating carriage pulling the drive electrical cables which are connected to rotate the RF loop cutter, and conducting a separate independent RF electrical signal to a different side of the RF loop cutter with each drive electrical cable.

In one embodiment, the probe is inserted by energizing a tunneling electrode, and the probe cuts around the specimen by energizing a rotational cutting electrode, with each of the two electrodes being energized independently of the other electrode. Alternatively, a single cutting electrode can be used to provide both tunneling cutting and circular cutting.

In a first embodiment wherein the RF loop cutter has a semicircular shape, positioning the semicircular shaped RF loop cutter flat relative to the direction of insertion of the RF probe during insertion of the RF probe. In a second embodiment wherein the RF loop cutter has a semicircular shape, positioning the semicircular shaped RF loop cutter orthogonally relative to the direction of insertion of the RF probe during insertion of the RF probe. In an alternative embodiment, rotating a worm gear drives a gear attached to the RF loop to rotate the RF loop.

BRIEF DESCRIPTION OF THE DRAWINGS

The present invention for an RF loop probe and method of excision and removal of breast lesions may be more readily understood by one skilled in the art with reference being had to the following detailed description of several preferred embodiments thereof, taken in conjunction with the accompanying drawings wherein like elements are designated by identical reference numerals throughout the several views, and in which.

DETAILED DESCRIPTION OF THE DRAWINGS

Figure 1:
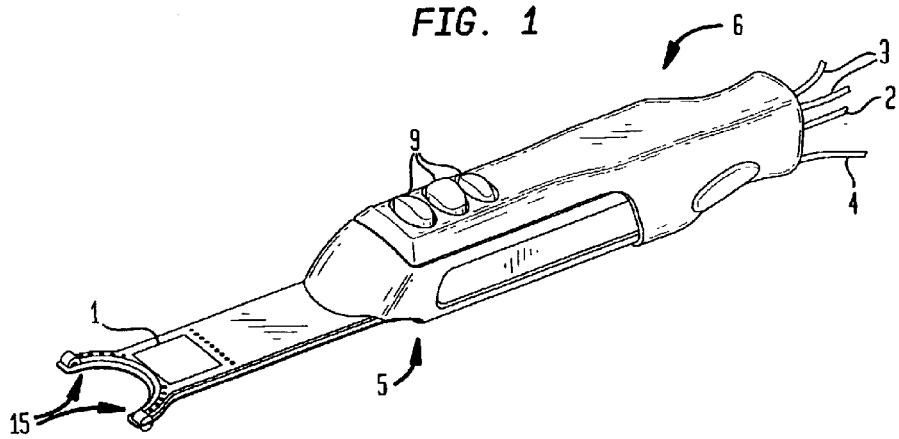
FIG. 1 is an isometric view of a first embodiment of a one-piece percutaneous lumpectomy device of the present invention showing the disposable probe mounted in the handpiece.

Referring to the drawings in detail, FIG. 1 is an isometric view of a first embodiment of a one-piece percutaneous lumpectomy device having a disposable probe 5 mounted in a handpiece 6. An RF loop 15 can operate in a monopolar configuration, or a ground pad 1 can be attached to the disposable probe 5 in a bipolar configuration, so that current only dissipates through the breast. A mechanical cable 2 is attached to the proximal end of the device to supply mechanical power to the probe. Two electrical wires 3 provide a separate RF electrical signal to each of the two blade components as described below. A ground wire 4 can be attached to the ground pad 1, which provides an RF current return path from the RF electrode blades 18 and 19, and connects to the ground of an RF generator (not shown).

Figure 2:
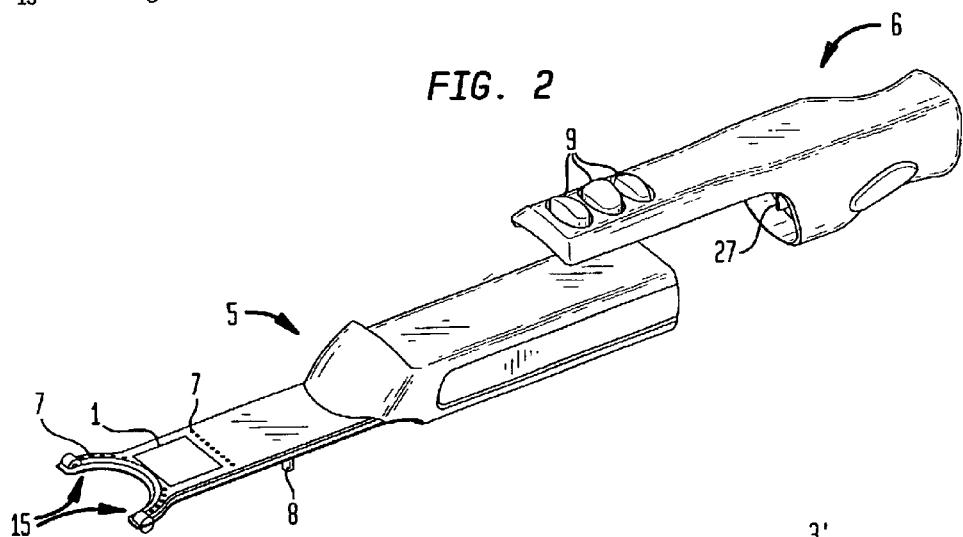
FIG. 2 shows the disposable probe separated from the reusable handpiece.
Figure 3:
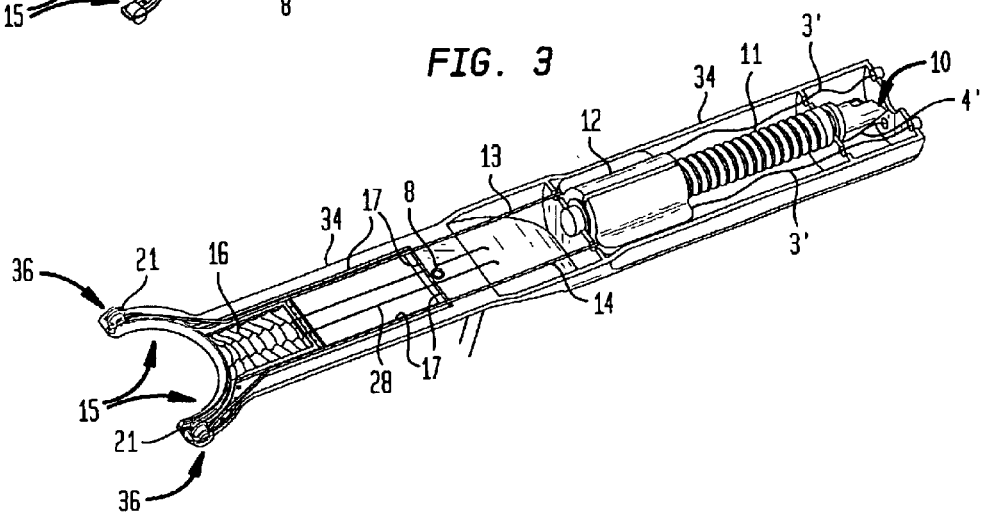
FIG. 3 shows a cut away view of the disposable probe and shows a shaft engagement, lead screw and carriage used to actuate the cable and spool mechanism.

The device operates as follows. Referring to FIGS. 1, 2, and 3, the cable 2 rotates a shaft having a rotatable engagement 27 on the handpiece 6, which engages a rotatable engagement 10 on the disposable probe 5 which rotates a lead screw 11. The rotating lead screw 11 axially translates carriage 12 from its distal position shown in FIG. 3 to a proximal position at the other end of lead screw 11. The translating carriage 12 pulls drive cables 13, 14, which are connected through spools 21 to rotate the RF loop 15.

FIG. 2 shows the disposable probe 5 separated from the reusable handpiece 6. Vacuum holes 7 are used to pull breast tissue and blood toward the device, to aspirate blood and to provide counter traction or immobilization to the adjacent tissue as the RF loop 15 rotates. A vacuum port 8 is located on the underside of the device for connection to a vacuum source. Electrical button switches 9 on the handpiece are used to energize and rotate the RF blade and to control the vacuum source. The rotational engagement shaft 27 for the lead screw is pictured on the reusable handpiece 6.

FIG. 3 is a cut away view of the disposable probe 5 with its top housing removed, and illustrates the bottom housing 34 in which is mounted the shaft engagement 10, the lead screw 11 and the carriage 12. The housing carries two RF electrical wires 3' which are connected to and are extensions of the two RF electrical wires 3, and a ground wire 4' which is connected to and is an extension of the ground wire 4, as illustrated generally in FIG. 16.

Figure 4:
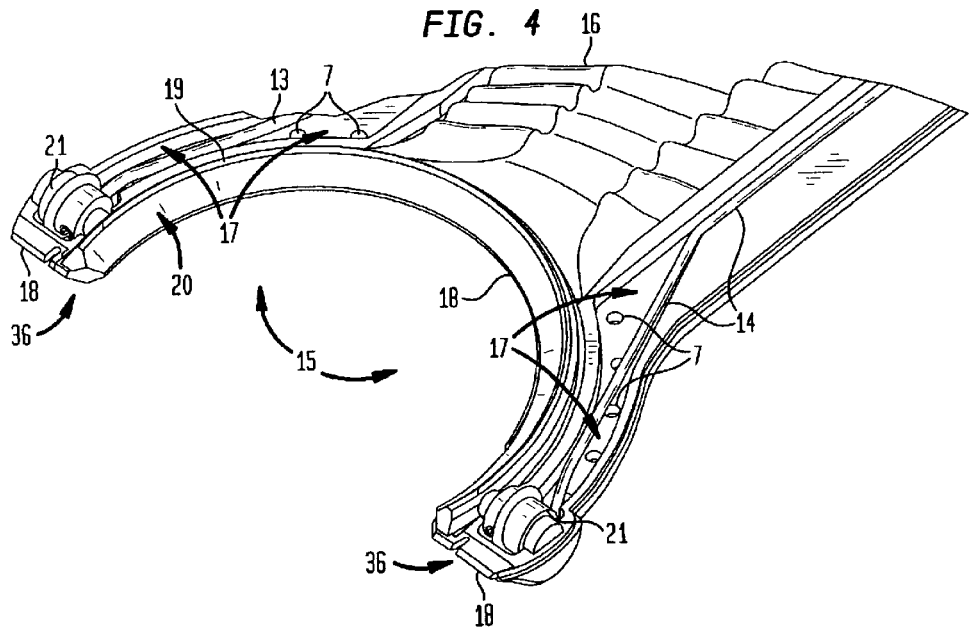
FIG. 4 is an enlarged view of the blade showing the two discrete RF electrodes, one for tunneling and one used during rotation of the blade.
Figure 5:
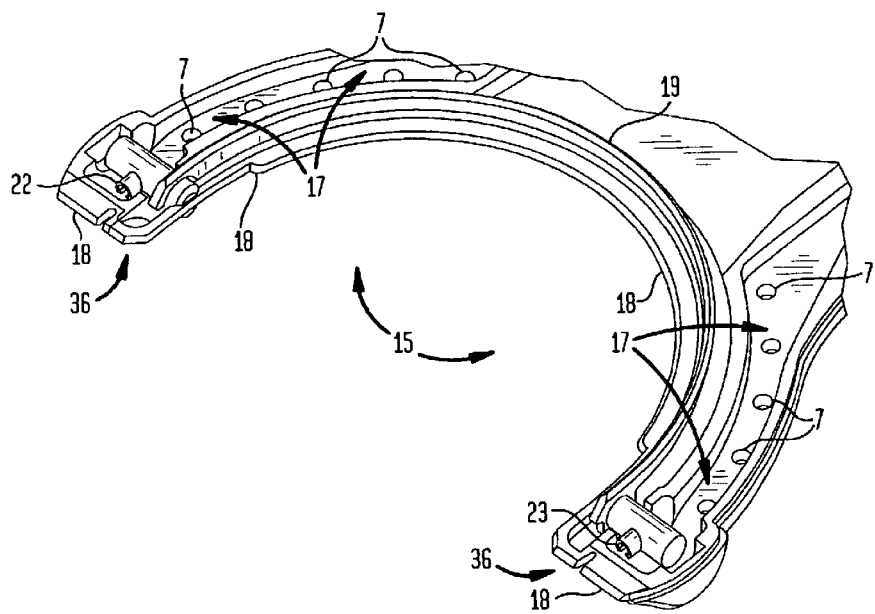
FIG. 5 is an enlarged view of the two independent RF electrodes without the insulating material therebetween, and the attachment points of the RF cables to the spools.

Referring to FIGS. 3, 4 and 5, the carriage 12 is used to pull drive electrical cables 13, 14 to rotate a pair of spools 21 attached to spaced and opposed legs 36 of the RF loop 15. The mechanical drive electrical cables 13, 14 are also insulated wires which conduct independent RF energy electrical signals from wires 3, 3 and 3', 3' to opposite sides of the RF loop 15. One cable 13 is connected to a first of the RF electrical wires 3' and energizes a tunneling electrode blade 18, and the other cable 14 is connected to a second of the RF electrical wires 3' and energizes a rotational electrode blade 19, as illustrated in FIGS. 4 and 5. The tunneling electrode blade 18 extends along all leading edges of the probe during insertion, including a concave curved leading edge of the RF loop and leading edges at the front of each opposed leg 36.

A specimen containment sheath 16 is stored adjacent to the RF loop 15 within the disposable probe 5 and is attached to the RF loop 15. The specimen containment sheath 16 is pulled by the RF loop 15 from its stored position illustrated in FIGS. 3 and 4 to its deployed position shown in FIGS. 9 and 12 as the RF loop is rotated in a circle, as shown sequentially in FIGS. 6–9. The disposable probe also defines a vacuum port 8 and channels 17 extending from the vacuum port 8 to the distal end of the disposable probe 5.

FIG. 4 is an enlarged view of one half of the housing supporting the rotationally moveable RF loop 15. The rotationally moveable RF loop 15 mounts a blade comprised of two discrete RF electrodes, a tunneling electrode 18 having an energized cutting edge in the lead direction of insertion of the probe 5, and a rotational cutting electrode 19 having an energized cutting edge in the lead direction of rotation of the RF loop. The electrode blades 18, 19 are bonded with an insulating material 20 between them so that each of the two electrodes 18,19 can be energized independently of the other. Nonconductive coatings, e.g. ceramic or plastic, may be used to focus current along cutting edges of the electrosurgical blade to minimize the power output requirements of the generator.

Two diametrically-opposed spools 21 are rigidly attached to the two diametrically-opposed legs 36 on opposite sides of the RF loop 15, and are attached to the cables 13, 14 and rotate the RF loop blade 15 as the electrical drive cables 13, 14 are drawn proximally by the translating carriage 12.

FIG. 5 is an enlarged view of the second half of the housing supporting the rotationally mounted blade 15, and shows the two independent RF electrodes 18, 19 without the insulating material 20 therebetween, and the two attachment points 22, 23 of the RF electrical cables to the spools. As illustrated in FIGS. 4 and 5, the electrical drive cable 13 is electrically connected to the tunneling electrode 18 by the connector 22, and the electrical drive cable 14 is electrically connected to the rotational cutting electrode 19 by the connector 23.

FIGS. 4 and 5 also illustrate the vacuum channels 17 which connect to the vacuum port 8 (see FIG. 2), and which also carry the movable drive electrical cables 13,14, FIG. 4, and lead to vacuum holes 7 to provide suction for the instrument.

Figure 6:
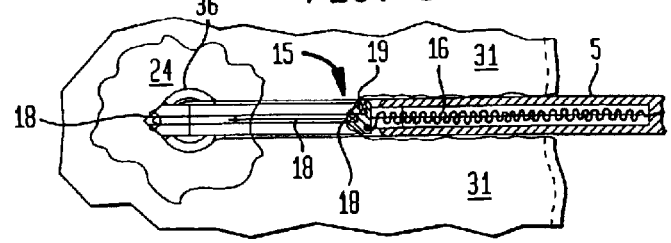
FIG. 6 is a cross-sectional view of the probe approaching a lesion in a breast wherein the RF loop is positioned proximal to the lesion, and the containment bag is connected to the RF loop and stored within the probe housing.
Figure 11:
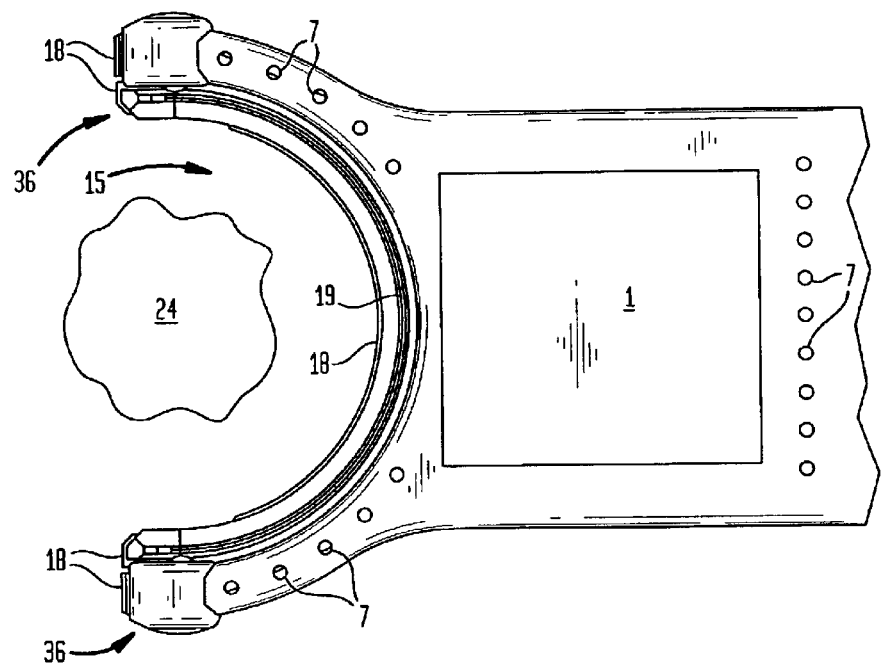
FIG. 11 is a top view of the device in the same position as FIG. 6, where the probe has approached and is positioned around a lesion in the breast.

FIG. 6 is a cross-sectional view of the probe inserted into surrounding breast tissue 31 and approaching a lesion 24 in the breast. The RF loop 15 is positioned proximal to the lesion 24 with the legs 36 of the RF loop straddling the lesion, as shown in FIGS. 6 and 11, and the containment sheath 16 is attached to the RF loop 15 and stored within the device as shown in FIGS. 3 and 4.

Figure 7:
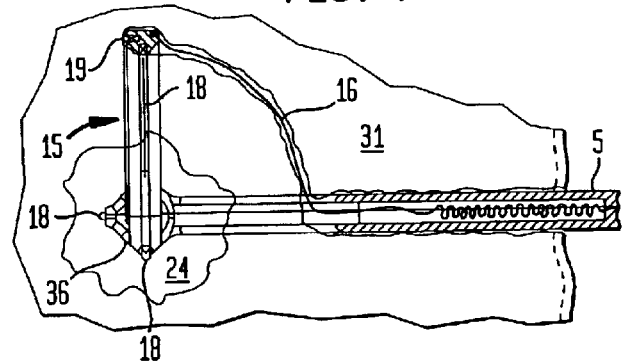
FIG. 7 is a cross-sectional view of the probe after the RF loop has been rotated 90 degrees, and shows the containment bag being pulled by the RF loop as it is rotated.

FIG. 7 is a cross-sectional view of the probe after the RF loop 15 has been rotated 90 degrees, and shows the lead edge of the containment sheath 16 being pulled by the RF loop 15 as it is rotated behind the cutting rotational electrode, and also illustrates the rotationally changed positions of the tunneling electrode 18 and the rotational cutting electrode 19.

Figure 8:
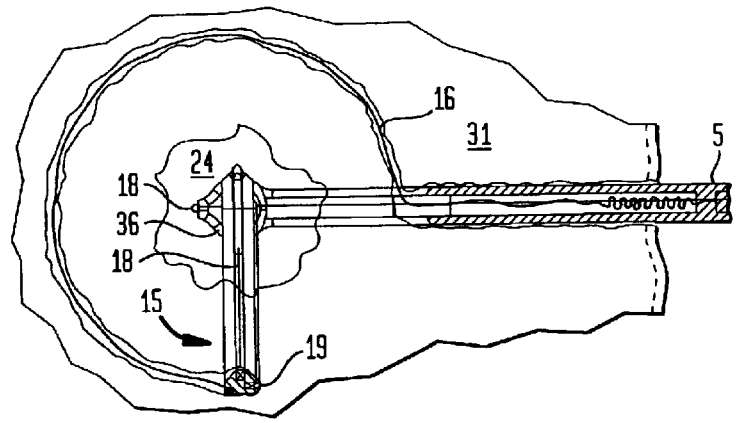
FIG. 8 is a cross-sectional view of the probe after the RF loop has been rotated 270 degrees, and shows more of the containment bag being pulled by the RF loop as it is rotated.

FIG. 8 is a cross-sectional view of the probe after the RF loop 15 has been rotated 270 degrees, and shows the containment sheath 16 being pulled by the RF loop 15 as it is rotated, and also illustrates the rotationally changed positions of the tunneling electrode 18 and the rotational cutting electrode 19.

Figure 9:
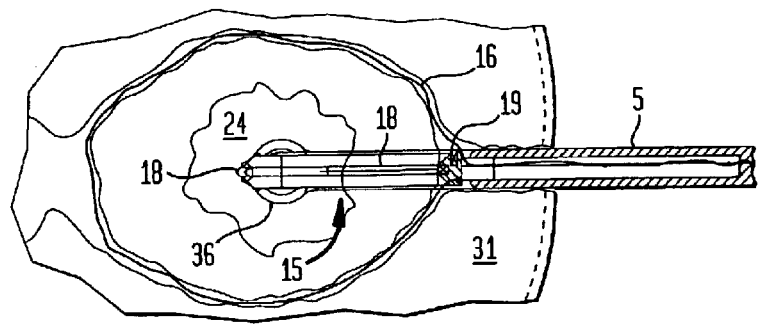
FIG. 9 is a cross-sectional view of the probe after the RF loop has been rotated 360 degrees and has completed the excision, and shows the containment bag surrounding the lesion and its partial removal from the breast.

FIG. 9 is a cross-sectional view of the probe after the RF loop 15 has been rotated 360 degrees and has completed the excision, and shows the containment sheath 16 surrounding the lesion 24 and its partial removal from the breast, and also illustrates the rotationally changed positions of the tunneling electrode 18 and the rotational cutting electrode 19.

Figure 10:
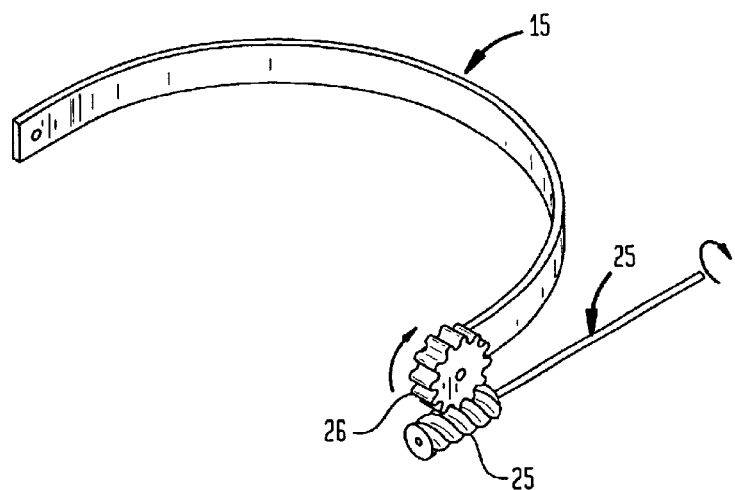
FIG. 10 shows an alternative embodiment of a rotational drive wherein a worm gear is rotated and drives a gear attached to an RF loop to rotate the RF loop either clockwise or counterclockwise.

FIG. 10 shows an alternative embodiment of a rotational drive wherein a worm gear 25 is rotated and drives a gear 26 attached to an RF loop 15 to rotate the RF loop either clockwise or counterclockwise, and for clarity of illustration eliminates other features.

FIG. 11 is a top view of the excisional biopsy device in the same position as FIG. 6, where the probe has approached, and the legs 36 of the probe are positioned on opposite sides of a lesion 24 in the breast. FIG. 11 also illustrates the vacuum operaures 7, and details of the tunneling electrode 18 having a concave curved leading edge extending around the inside of the RF loop 15 and also extending along the fronts of the legs 36 and the RF loop 15.

Figure 12:
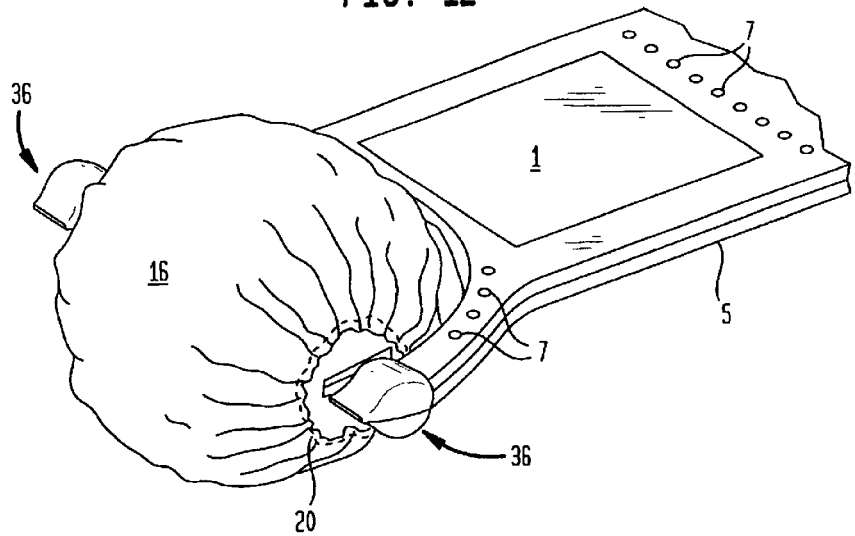
FIG. 12 show the probe after the tissue has been excised and the containment bag is fully deployed. A draw cord is used to cinch the two ends of the bag to hold the tissue specimen in place and to prevent cancer cell displacement during removal.

FIG. 12 show the probe after the tissue has been excised and the containment sheath 16 is fully deployed. A draw cord 28 is used to cinch the two ends of the bag to hold the tissue specimen securely in place in the bag and to prevent cancer cell displacement during removal of the sheath.

Figure 13:
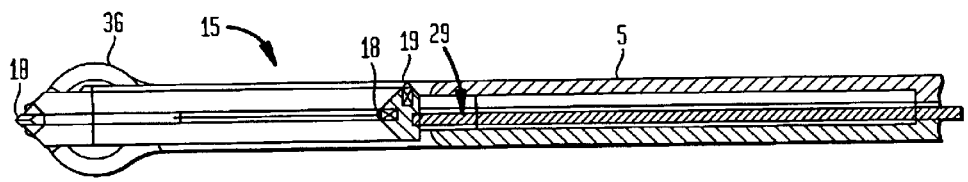
FIG. 13 shows a pin which holds the blade in place during tunneling, and which can be pulled proximally to release the blade to rotate and excise the specimen.

FIG. 13 shows a pin 29 which is used to hold the RF loop blade 15 in place during tunneling, and which can be pulled proximally to release the blade 15 to rotate and excise the specimen, and also shows different portions of the RF blade electrodes 18, 19.

Figure 16:
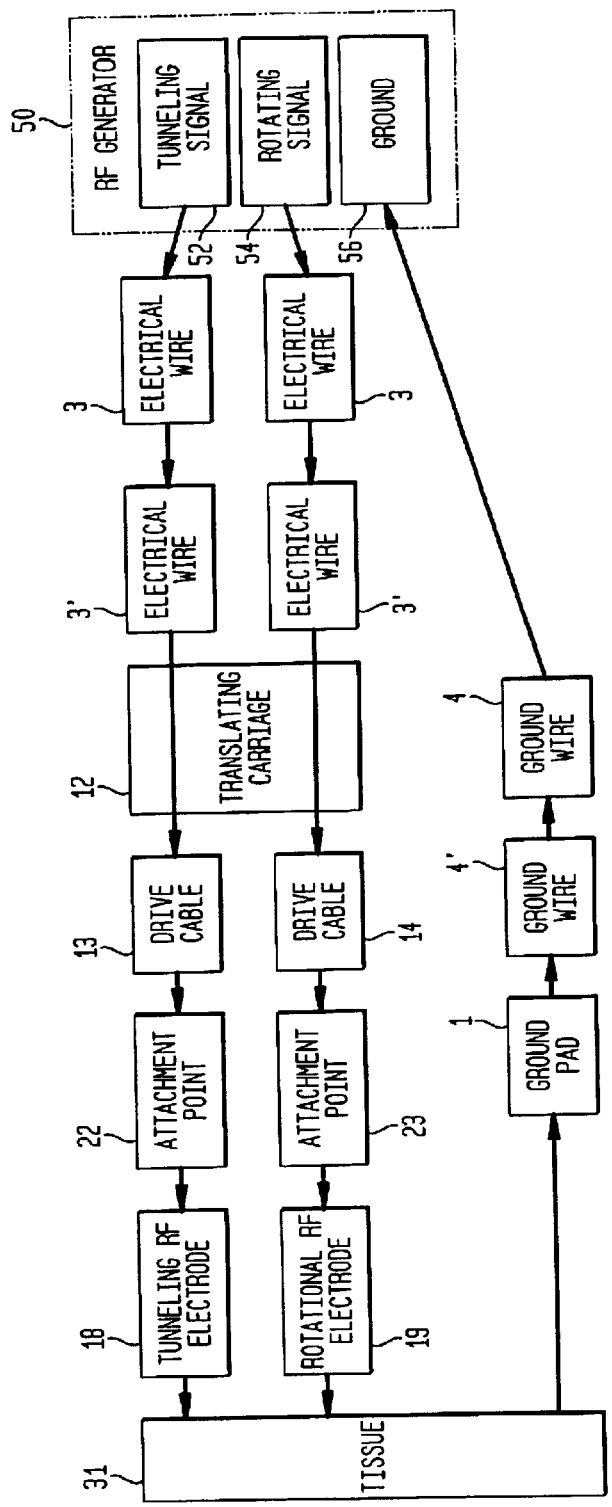
FIG. 16 is a simplified electrical diagram which illustrates an RF generator and the RF electrical connections through the instrument to the RF tunneling and rotational electrode blades.

FIG. 16 is a simplified electrical diagram which illustrates an RF generator 50, which includes a tunneling RF signal generator 52, a rotating RF signal generator 54, and a ground 56. FIG. 16 also illustrates the RF electrical connections through the wires 3, 3, through the wires 3', 3', through the translating carriage 12, through the drive electrical cables 13, 14 to the attachment points 22, 23 to the RF electrode blades 18, 19, through the surrounding tissue 31 of the patient, through the ground pad 1, through the ground wire 4', through the ground wire 4, and back to the ground 56 of the RF generator 50.

Figure 14:
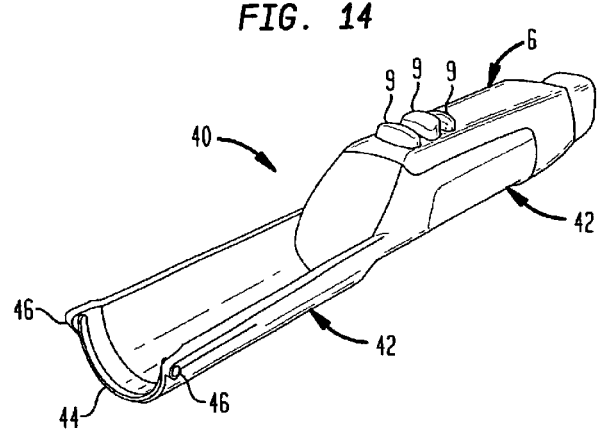
FIG. 14 is an isometric view of a further embodiment of a one-piece percutaneous lumpectomy device of the present invention having a disposable probe which, from an end view, defines a generally semicircular, arcuate cross section.
Figure 15A:
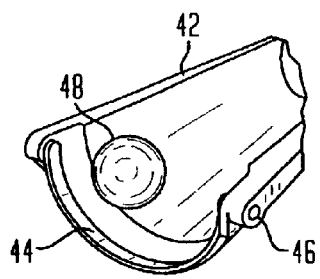
FIGS. 15A, 15B, 15C and 15D illustrate consecutive 90 degree displaced positions of the RF blade as it is rotated to excise a selected specimen of tissue.
Figure 15B:
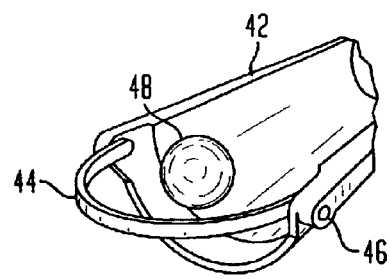
Figure 15C:
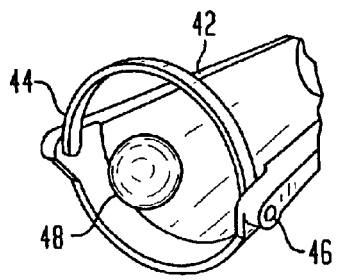
Figure 15D:
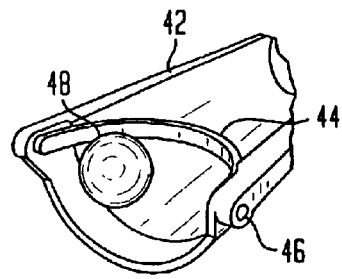

FIG. 14 is an isometric view of a further embodiment of a one-piece percutaneous lumpectomy device 40 of the present invention having a disposable probe 42 which, from an end view, defines a generally semicircular, arcuate or C shaped cross section. A single RF blade 44 is pivotally mounted at opposed pivots 46 on opposite sides of the end of the probe, with FIG. 14 illustrating the RF blade in the position in which the probe is inserted into a patient while making a generally semicircular incision in the patient. The device 40 is only shown conceptually and schematically in FIGS. 14 and 15, and so a specimen containment sheath similar to sheath 16 is not illustrated therein, but would be present on a more detailed illustration thereof, and would be deployed in a manner similar to that illustrated in FIGS. 6–9.

This embodiment of the present invention employs an arcuate tunneling blade, and a single element provides cutting during both tunneling and cutting. The procedural steps of this embodiment are similar to the first embodiment. The incision length of this embodiment is approximately 1.5 times longer than the first embodiment, but may result in reduced tunneling forces and less need for tissue retraction as the sphere of tissue is being cut.

FIGS. 15A, 15B, 15C and 15D illustrate consecutive 90 degree displaced positions of the RF blade 44 as it is rotated to excise a selected specimen 48 of tissue. Although not illustrated by the conceptual drawings of FIG. 14, the rotating RF blade would deploy a containment bag as it is being rotated, in a manner similar to the previously described embodiments.

The present invention provides a device and method for excision and removal of neoplasms under real-time image guidance with minimal disruption of normal tissue while providing an optimal specimen to assess the completeness of the excision. The device and method are minimally invasive, and are used to remove cancerous lesions from soft tissue, including breast tissue, and are a less invasive alternative to open lumpectomy. The invention provides an RF loop for excision and removal of breast lesions which promotes hemostasis during excision through electrosurgical coagulation of blood vessels and channels to supply pressure and hemostatic fluids to the tissue cavity.

The present invention is used with the following procedural steps. The mass is localized, and the tunneling trajectory is determined. The skin is excised, and tunneling is begun by activating and using the semi-circular RF tunneling electrode 18. After tunneling is completed, but prior to cutting a sphere, the coordinates of the excision specimen 24 are confirmed, preferably with the assistance of computer aided imaging and guidance technology. The semi-circular rotational electrode blade 19 of the RF loop is then activated and used to cut the sphere, and is rotated by the drive electrical cables 13, 14 attached to the power drive 2, 27, 10, 11 and 12. Simultaneously, the tissue is immobilized and any blood is aspirated with the vacuum 8 and vacuum ports 17. As the RF loop 15 is rotated, it pulls along the containment sheath or bag 16 that surrounds the spherical specimen 24. After the sphere is fully cut, the RF loop 15 is held in place and the containment sheath 16 is pulled taught around the sphere by the draw cord 28 to reduce the sphere's volume to aid in its removal. The device and sphere are then removed from the body simultaneously.

The present invention has the following clinical benefits: minimally invasive, real-time control and flexibility, and removal of a god specimen for pathological evaluation.

Minimally Invasive

The present invention provides an efficient excision volume, i.e. sphere, without cutting through the lesion. A spherical excision volume is generally preferred to alternative excision volumes provided by some prior art approaches, such as conical or cylindrical excision volumes. By tunneling with a flat blade, the tissue between the skin and lesion is preserved for improved cosmesis and hemostasis, especially for lesions located deep in the breast. Less tissue is taken because the procedure is an image-guided procedure, the tunnel can be small, and access is not required for hands and a scalpel.

Real-time Control and Flexibility

Multiple passes are possible with different sized electrosurgical cutting electrodes to shave additional margins. Computer aided imaging and guidance assist in planning the excision and provide real-time feedback and guidance. The device can be used in a hand-held manner with real-time imaging, with most likely ultrasound or quasi-real-time MRI assisting the surgeon to more accurately assess the desired excision volume. The device may be used in a fixed configuration, such as attached to a stereotactic x-ray machine. The device eliminates the needle localization procedure. A more flexible system makes it easier to remove the entire cancer than with a prior art device.

Removal of a Good Specimen for Pathological Evaluation

The present invention provides one piece removal, and doesn't cut through the lesion, preserving the specimen orientation.

The following are system technical features associated with the present invention: optimization of RF energy, channels for vacuum and fluid delivery, and specimen containment sheath.

Optimization of RF Energy

The diamond blade cross-section focuses maximum power density along the cutting edges of the electrosurgical blade, thereby minimizing the power the generator must output to effectively cut and coagulate the tissue. Nonconductive coatings, e.g. ceramic or plastic, may be used to focus current along cutting edges of the electrosurgical blade to minimize the power output requirements of the generator. Electrosurgical cutting promotes hemostasis, especially compared to mechanical cutting. Feedback control may be employed during cutting to monitor tissue electrical, thermal and/or optical properties, such as the tissue impedance, and to modify the power output to match the tissue parameters. A return electrode may be located on the device to provide a bipolar configuration, thereby preventing current from flowing beyond the breast, as in a monopolar configuration. The current, voltage, and power curve of the generator is preferably optimized to match the tissue impedance seen by the loop to most effectively use the power output of the generator.

Channels for Vacuum and Fluid Delivery

Vacuum channels on the device provide counter traction during cutting of a specimen. Vacuum channels are used to aspirate blood and to prevent coagulation through a vacuum system. Positive pressure may be applied to the cavity through the same channels for hemostasis and to aid in imaging the cavity. Fluids containing hemostatic and ultrasound contrast agents may be injected into the cavity through the channels for hemostasis and to aid in imaging the cavity.

Specimen Containment Sheath

The cutting element deploys a containment sheath or bag around the tissue specimen to prevent displacement of cancer cells into the surrounding tissue. Then containment sheath contains the tissue specimen during removal, allowing some compression of the sample. This compression decreases the size of the skin incision required to remove the specimen.

While several embodiments and variations of the present invention for an RF loop probe and method of excision and removal of breast lesions are described in detail herein, it should be apparent that the disclosure and teachings of the present invention will suggest many alternative designs to those skilled in the art.

What is claimed is:

1. A medical device for removal of a lesion from tissue comprising:

a probe housing, the probe housing having a longitudinal axis;

a rotatable cutter mounted at the distal end of the probe housing, wherein the rotatable cutter is mounted for rotation about an axis substantially perpendicular to the longitudinal axis of the probe housing, and wherein the cutter comprises at least one electrode;

a drive for rotationally driving the cutter around a tissue specimen containing the lesion;

a specimen containment sheath adapted to be deployed by the cutter as it is rotated to perform a rotational cut, such that the specimen containment sheath is drawn around the tissue specimen as the cutter cuts around the specimen.

2. The device of claim 1, wherein the drive comprises first and second cables which are mechanically displaced to rotate the cutter, and wherein the cables also conduct RF electrical signals to the cutter.

3. The device of claim 1, wherein the cutter comprises a generally semicircular RF loop cutter which cuts a generally spherical tissue specimen.

4. The device of claim 1 comprising a drawstring pulling the containment sheath around the tissue specimen.

5. The device of claim 1 adapted for flow communication with a source of vacuum.

6. The device of claim 1 comprising vacuum channels formed therein.

7. The device of claim 1 comprising at least one drive electrical cable housed in at least one vacuum channel.

8. The device of claim 1 comprising a disposable probe portion associated with a reusable handpiece.

9. The device of claim 1 wherein the probe housing comprises opposed legs and wherein the cutter is disposed for rotation between the opposed legs.

10. The device of claim 1 wherein the cutter comprises at least two electrodes.

11. The device of claim 10 wherein the two electrodes are energized independently of each other.

12. The device of claim 1 wherein the cutter comprises a single cutting electrode for tunneling and rotational cutting.

* * * * *